United States Patent [19]
Cairns et al.

[11] Patent Number: 6,054,480
[45] Date of Patent: Apr. 25, 2000

[54] FATTY ACIDS AS A DIET SUPPLEMENT

[75] Inventors: Charles B. Cairns, Denver; Keith E. Hampton, Telluride, both of Colo.

[73] Assignee: Nectra, Inc., Telluride, Colo.

[21] Appl. No.: 08/932,457

[22] Filed: Sep. 18, 1997

[51] Int. Cl.⁷ ............................ A61K 31/19; A61K 31/20
[52] U.S. Cl. ............................................ 514/557; 514/558
[58] Field of Search ....................................... 514/557, 558

[56] References Cited

FOREIGN PATENT DOCUMENTS

| | | | |
|---|---|---|---|
| 0303523 | 2/1989 | European Pat. Off. | ...... C07C 69/675 |
| 3217071 | 11/1983 | Germany | .......................... A61K 9/22 |
| 04325055 | 11/1992 | Japan . | |

OTHER PUBLICATIONS

Björntorp et al., "Albumin Antagonism of Fatty Acid Effects on Oxidation and Phosphorylation Reactions in Rat Liver Mitchondria", J. Biol. Chem., 239(1):339–344 (1964).

Bucalossi et al., "Relationship Between Fatty Acids of Adipose Tissue and Plasma Cholesterol", Gerontol. Clin. (Basel), 17(4):204–209 (1975).

Bradley, "Endotoxic Activity of Complexes of Myristic Acid and Proteins", Proc. Soc. Exp. Biol. Med., 151(2):267–270 (1976).

DeGrella et al., "Uptake and Metabolism of Fatty Acids by Dispersed Adult Rat Heart Myocyte (I)", J. Biol. Chem., 255(20):9731–9738 (1980).

DeGrella et al., "Uptake and Metabolism of Fatty Acids by Dispersed Adult Rat Heart Myocytes (II)", J. Biol Chem., 255(20):9739–9745 (1980).

Gröning et al., "Dosage Forms with Controlled Gastrointestinal Passage –Studies on the Absorption of Nitrofurantoin," Int'l Journal of Pharmaceutics, 56:111–116 (1989).

Hughes et al., "Comparative Lipoprotein Metabolism of Myristate, Palmitate, and Stearate in Normolipidemmic Men", Metabolism: Clin & Exp., 45(9): 1108–1118 (1996).

Lehninger, "The Relationship of the Adenosine Polyphosphates to Fatty Acid Oxidation in Homogenized Liver Preparations", pp. 363–381.

Mensink et al., "Effect of Dietary Trans Fatty Acids on High–Density and Low–Density Lipoprotein Cholesterol Levels in Healthy Subjects" New. Engl. J. Med., 323(7):439–445 (1990).

Pressman et al., "Effect of Surface Active Agents on the Latent ATPase of mitochondria", 21:458–467 (1956).

Tholstrup et al., "Acute Effect of High–Fat Meals Rich in Either Stearic or Myristic Acid on Hemostatic Factors in Healthy Young Men," Am. J. Clin. Nutr., 64(2):168–176 (1996).

Stucki et al., "Acylation of Proteins by Myristic Acid in Isolated Mitochondria", J. Biol. Chem., 264(11):6376–6380 (1989).

Temme et al., "Effects of Medium Chain Fatty Acids (MCFA), Myristic Acid, and Oleic Acid on Serum Lipoproteins in Healthy SubjEcts," Journal of Lipid Research, 38:1746–1754 (1997).

Tove et al., "Toxicity of Rac–1(3)–Myristoyl Glycerol to Mice", J. Nutr. 118:1463–1469 (1988).

Wolf et al., "The Cost of Obesity—The US Perspective", PharmacoEconomics, 5(Suppl. 1):34–37 (1994).

Groening et al —Int. J. Pharm., 56(2), 111–116 (Abstract) 1989.

Temme et al. —J. Lipid Res., 38(9), 1746–54 (Abstract) 1997.

Primary Examiner—Zohreh Fay
Attorney, Agent, or Firm—Townsend and Townsend and Crew LLP

[57] ABSTRACT

Compositions containing a $C_{12}$–$C_{15}$ fatty acid or a derivative thereof are provided along with methods which use those compositions for controlling or reducing a subject's weight.

18 Claims, No Drawings

FATTY ACIDS AS A DIET SUPPLEMENT

BACKGROUND OF THE INVENTION

Nutritional substrates include fats, proteins and sugars which are used for energy in the human body. The body stores excess energy until it is needed for energy production. Most of the long term storage is in the form of body fat. The balance between energy storage and energy utilization determines the fat content, a key component of body weight. The three components of energy expenditure are resting metabolism, physical activity and thermogenesis.

Oxygen is needed for the efficient cellular utilization of these energy stores and thermogenesis. Over 90% of cellular oxygen is consumed by mitochondria for the process of ATP formation, which is known as oxidative phosphorylation. Adenosine triphosphate (ATP) is the main high energy cellular substrate and is used for both cellular maintenance reactions (e.g., electrolyte balance and signal processing) and active processes (e.g., muscle contraction and protein synthesis).

The body is dependent upon mitochondrial oxidative phosphorylation for the efficient production of ATP. For example, for each molecule of glucose, 36 molecules of ATP are produced if mitochondrial oxidative phosphorylation is fully utilized whereas only 2 molecules of ATP are produced without mitochondrial processing.

Because ATP occupies such a central role in energy use/processing and due to the bodies dependence on mitochondria for the production of ATP, almost all nutritional substrates (including fats) are processed by cellular and mitochondrial enzymes (i.e., dehydrogenases) into the high energy electron carriers, NADH and $FADH_2$. Each of these molecules delivers electrons to the respiratory chain of mitochondria located in the inner mitochondrial membrane. These electrons are passed down the respiratory chain and eventually placed onto oxygen via the enzyme cytochrome oxidase. As the electrons are passed down the respiratory chain, protons are extruded across the inner mitochondrial membrane which results in the formation of a proton gradient. The electrical and chemical energy of the proton gradient across the inner membrane is then used to create ATP in the process known as oxidative phosphorylation.

The body produces a substance that directly affects the efficiency of mitochondrial oxidative phosphorylation. This substance is known as thermogenin, which is a protein found in brown fat cells (so named due to the abundance of mitochondria in these cells). Thermogenin uncouples the production of ATP from electron transport and oxygen consumption. Thus, energy is consumed but is not utilized for energy production in these cells. Accordingly, uncoupling energy utilization from energy production could result in weight loss.

It has been found that patients with morbid obesity have less brown fat than patients of normal weight (see Himms-Hagen, *Canadian J. Biochem. & Cell Biol.*, 62(7):610–617 (1984) and Santos, *Arch. Path. & Lab. Med.* 116(11):1152–1154 (1992)). Efforts to utilize the endogenous protein thermogenin to directly alter metabolism and body weight have not been successful, presumably due to low transport into cells and mitochondria. Other chemicals could potentially affect the efficiency of oxidative phosphorylation in a manner similar to thermogenin. However, most of these leads are proteins which are not easily absorbed after oral administration. Additionally, such agents are not well transported intracellularly as needed for biological activity.

Others efforts to chemically lower body weight by indirectly altering cellular energy metabolism have used hormones such as leptin and serotonin. These hormones are thought to indirectly alter the efficiency of energy metabolism and have not been demonstrated to have direct effects on oxidative metabolism. These hormones have other significant physiologic effects (e.g., elevated heart rate, elevated blood pressure, behavioral swings) beyond their effects on metabolism. Still further, some of these proposed mediators of obesity must be given parenterally.

What is needed in the art are new compositions and methods for controlling weight using safe agents which are readily absorbed after oral administration and which do not suffer the poor side effects and activity associated with the agents described above. Surprisingly, the present invention provides such compositions and methods.

SUMMARY OF THE INVENTION

The present invention provides a composition for reducing the weight of a subject as well as methods for dieting, reducing weight or maintaining weight using the compositions provided herein. The present compositions comprise a weight-reducing amount or weight-maintaining amount of a $C_{12}$–$C_{15}$ fatty acid, metal or pharmaceutical salts of a $C_{12}$–$C_{15}$ fatty acid, or biological precursors of a $C_{12}$–$C_{15}$ fatty acid, typically in combination with a pharmaceutically acceptable carrier. In one group of embodiments, the compositions are formulated for oral administration and will further comprise mannitol, lactose, starch, magnesium stearate, sodium saccharin, glucose, sucrose, magnesium carbonate, or combinations thereof. Preferably, the compositions are incorporated into food products or are in unit dosage form in tablets, pills, or capsules.

DETAILED DESCRIPTION

General

The present invention derives from the surprising discovery that certain fatty acids are transported intracellularly to the mitochondria and alter oxidative metabolism, thereby causing weight loss. Traditionally, fatty acids have been considered by nutritionists to be weight enhancing agents and potentially detrimental as nutritional supplements.

Studies of the thermodynamic efficiency of oxidative metabolism provided the basis for the present invention. As a result of these studies, it was felt that certain fatty acids could directly alter the coupling of oxidative metabolism. Additionally, the fatty acids described herein were thought to possess the desired physical properties to be membrane permeable when administered exogenously. In view of these initial studies and the detailed experiments below, myristic acid has now been identified as a biologically active agent for inducing weight loss.

Beyond weight enhancing effects, clinical research on myristic acid and nutrition has focused on an association between myristic acid and the development of atherosclerotic heart disease. Epidemiologic reports have also suggested that diets high in myristic acid and other saturated fatty acids can lead to hypercholesterolemia and atherosclerosis (see, Buccalossi, et al., *Geron. Clin.* 17(4):204–209 (1975)). This view continues to be promulgated by some nutritionists (see, Kromhout, et al., *Prev. Med.* 24(3):308–315 (1995)).

Still other studies on fatty acids have indicated that the acids can be metabolized differently. Thus, it is incorrect to regard all saturated fatty acids as metabolically similar in clinical studies (see Hughes, et al., *Metabolism: Clinical & Experimental* 45(9):1108–18 (1996)). For example, myristic acid has been shown to cause slight increases in the beneficial high density lipoproteins (HDLs) while not being more cholesteremic than other fatty acids (see, Tholsthrup, et al., *American Journal of Clinical Nutrition.*, 60(6) :919–925 (1994)). The effect of non-cholesterol raising trans unsaturated fatty acids on the serum lipoprotein profile is at least as unfavorable as that of the cholesterol-raising saturated fatty acids because the trans acids not only raise LDL cholesterol levels but also lower HDL cholesterol levels (see, Mensick, et al., *New England Journal of Medicine*, 323(7):439–45 (1990)). In related studies, the acute pro-thrombogenic effects attributed to diets high in saturated fatty acids, including myristic acid, have not been confirmed (see, Tholstrup, et al. *American Journal of Clinical Nutrition.*, 64(2):168–76 (1996)) for myristic acid.

The use of myristic acid as a food additive is known, albeit typically as an anticaking agent (World Health Organization, WIWI4H, No. 5, pp. 19–20 (1974)).

Embodiments of the Invention

In one aspect, the present invention provides a composition for reducing the weight of a subject. The composition comprises a weight-reducing amount of a $C_{12}$–$C_{15}$ fatty acid, a metal ion salt of a $C_{12}$–$C_{15}$ fatty acid, or a biological precursor of a $C_{12}$–$C_{15}$ fatty acid. In this aspect of the invention, the composition will typically include the a $C_{12}$–$C_{15}$ fatty acid or derivative thereof (e.g., a metal ion salt or biological precursor) in admixture with a pharmaceutically acceptable carrier or formulation components for oral administration. As used herein, the term "biological precursor" refers to any molecule which can be transformed in vivo into a $C_{12}$–$C_{15}$ fatty acid or a salt thereof. Typically, such transformation involve hydrolysis reactions (which can be mediated by acidic or basic conditions in vivo or by esterases or proteases) and redox reactions.

In one group of embodiments, a $C_{12}$–$C_{15}$ fatty acid and its biological precursors will be those expressed by formula I:

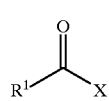

(I)

In this formula, $R_1$ is a hydrocarbon chain having a molecular length equivalent to a $C_{11}$ to $C_{14}$ fatty acid. The hydrocarbon chain can be saturated or unsaturated and will optionally contain additional lower alkyl substituents (e.g., methyl or ethyl). Preferably, the hydrocarbon chain will have a molecular weight of from about 140 to about 250 Daltons. The group X is —OH, —OR, NH$_2$, —NHR, —NRR', —NHOH, —NHOR, in which R and R' are each independently a lower alkyl group having from one to eight carbon atoms, either in a straight or branched chain. Additionally, R and R' can be combined to form a ring structure, for example, —NRR' can be a pyrrolidinyl or piperidinyl group, which is optionally substituted by additional lower alkyl ($C_1$–$C_4$) groups.

In preferred embodiments, X is —OH, —OR, —NH$_2$, or —NHR, in which R is methyl, ethyl, propyl, n-butyl, isobutyl or t-butyl. More preferably, X is —OH, —OCH$_3$, or —NH$_2$. Each of the compounds above are commercially available from chemical suppliers such as Aldrich Chemical Company (Milwaukee, Wis., USA) or Sigma Chemical Company (St. Louis, Mo., USA) or can be prepared from commercially available compounds using methods known to those of skill in the art. For example, N,N-diethyl myristamide can be prepared by converting commercially available myristic acid to an acid chloride (using, for example, oxalyl chloride), then treating the acid chloride with diethylamine and an additional equivalent of the amine or another suitable acid scavenger to form the target amide. Simple chromatographic methods can be used to purify the target compound.

Metal ion salts or pharmaceutical salts of a $C_{12}$–$C_{15}$ fatty acid which are useful in the present compositions can be prepared by treatment of the acid with either a cation exchange resin or alkaline/alkali hydroxide (e.g, NaOH, KOH, LiOH, CsOH, Mg(OH)$_2$, Ca(OH)$_2$). Alternatively, ammonium salts can be prepared and used in the present invention by treating the acid with ammonia or other primary, secondary or tertiary amines (e.g., methylamine, ethylamine, propylamine, diisopropylethyl amine, pyrrolidine, piperidine, pyridine, and the like).

A particularly preferred fatty acid in this aspect of the invention is myristic acid (or a metal ion salt or biological precursor of myristic acid).

The above fatty acids and their derivatives can be formulated for oral delivery in a variety of dosage forms. These include, for example, solid, semi-solid and liquid dosage forms, such as tablets, pills, liquid solutions or suspensions, and formulation which include carriers such as, for example, liposomes. These formulations will comprise a $C_{12}$–$C_{15}$ fatty acid or its derivative in a therapeutically or pharmaceutically effective dose (e.g. a weight-reducing amount or a weight-maintaining amount) together with one or more pharmaceutically or therapeutically acceptable carriers and optionally other therapeutic ingredients. As used herein, the term "weight-reducing amount" refers to an amount which, when administered according to a prescribed regimen, provides a reduction in weight of from about 0.5% to about 10% or more over the course of the treatment program. Preferably, the compositions will contain an amount sufficient to provide a reduction in weight of from about 2% to about 10% over the course of treatment. One of skill in the art will understand that precise amounts will be dependent on the subject's weight and age, as well as other health considerations. Typically, for humans, the amount of myristic acid will be from about 0.1 mg/kg per day to about 10,000 mg/kg per day, more preferably about 10 mg/kg per day to about 1000 mg/kg per day. At this dosage, the effects of myristic acid can reduce an individual's weight by about 0.5% to about 10% over about a 7 day to 30 day time period, if other dietary considerations are held constant.

Various formulation and administration considerations are described, e.g., in Gilman et al. (eds) (1990) GOODMAN AND GILMAN'S: THE PHARMACOLOGICAL BASES OF THERAPEUTICS, 8th Ed., Pergamon Press; NOVEL DRUG DELIVERY SYSTEMS, 2nd Ed., Norris (ed.) Marcel Dekker Inc. (1989), and REMINGTON'S PHARMACEUTICAL SCIENCES, the full disclosures of which are incorporated herein by reference. Methods for administration are discussed therein, e.g., oral, or alternatively intravenous administration and others. Pharmaceutically acceptable carriers will include water, saline, buffers, and other compounds described, e.g., in the MERCK INDEX, Merck & Co., Rahway, N.J. See, also, BIOREVERSIBLE CARRIERS IN DRUG DESIGN, THEORY AND APPLICATION, Roche (ed.), Pergamon Press, (1987). In still other embodiments, the active agent (whether a $C_{12}$–$C_{15}$ fatty acid or a derivative thereof) can be formulated in liposomes using any of the loading technologies known to those of skill in the art (e.g., passive entrapment, active loading via pH or other ion gradients).

For oral delivery, the formulation will often be in the form of a lozenge, tablet, or capsule. The method of manufacture of these formulations are known in the art, including but not limited to, the addition of the pharmacological agent to a pre-manufactured tablet; cold compression of an inert filler, a binder, and either a pharmacological agent or a substance containing the agent (as described in U.S. Pat. No. 4,806,356); and encapsulation.

In another aspect, the present invention provides a method for reducing weight in a subject in need thereof, the method comprising administering to the subject a composition comprising a weight-reducing amount of a compound selected from a $C_{12}$–$C_{15}$ fatty acid, metal ion salts of a $C_{12}$–$C_{15}$ fatty acid, and biological precursors of those acids. As used herein, the term "subject" refers to any animal, preferably mammal and more preferably human. In this aspect of the invention, myristic acid, its salts and derivatives are particularly preferred and have been described above.

The method of administration can be essentially any method used for pharmaceutical delivery including, for example, oral, intravenous, intramuscular, intraperitoneal, transcutaneous, intrathecal, and transmucosal. Preferably, administration is oral and the composition is formulated as a dietary supplement in unit dosage form in amounts which have been noted above.

In yet another aspect, the present invention provides a method of maintaining the weight of a subject having a high fat diet, the method comprising administering to the subject, a weight-maintaining amount of a compound selected from the group consisting of a $C_{12}$–$C_{15}$ fatty acid, metal ion salts of a $C_{12}$–$C_{15}$ fatty acid, and biological precursors of those acids.

In this aspect of the invention, the subjects and active agents are those which have been described above. As used herein, the term "weight-maintaining amount" refers to that amount which, when administered according to a prescribed regimen, allows a subject to maintain a desired weight within about 2%, and preferably within about 1% of their desired target weight. For example, a 150 lb individual having a high fat diet will be administered an amount which is sufficient to maintain the individual's weight in a range of from about 147 to 153 lbs, preferably about 148.5 to 151.5 lbs. Typically, the weight-maintaining amount of the agent or compound will be less than that for weight-reducing compositions. Nevertheless, the amount will vary depending on the subject and the subject's diet. Accordingly, for a subject having a high fat diet (e.g. a diet consisting of about 1.5 to 5 times the average daily fat intake for a human), the weight-maintaining amount of the active agent will be about 0.05 mg/kg per day to about 10 mg/kg per day, more preferably about 0.5 mg/kg per day to about 5 mg/kg per day.

In still another aspect, the present invention provides a method of dieting in a human, comprising ingesting a compound selected from the group consisting of a $C_{12}$–$C_{15}$ fatty acid, metal ion salts of a $C_{12}$–$C_{15}$ fatty acid, and biological precursors of those acids, in an amount of from about 0.05 mg per kg of the human per day to about 10,000 mg per kg of the human per day. The amounts provided for this aspect of the invention include the ranges for both weight-reducing amounts and weight-maintaining amounts as the dieting subject may elect to alternate in administering to themselves a first amount which is a weight-reducing amount, then a second amount which is a weight-maintaining amount, or vice versa. Preferably, the $C_{12}$–$C_{15}$ fatty acid is myristic acid and the biological precursors for myristic acid are the lower alkyl ($C_1$–$C_8$) esters of myristic acid, more preferably a methyl ester of myristic acid.

While the present invention has been described in some detail for the use of a $C_{12}$–$C_{15}$ fatty acid and its derivatives in pharmaceutical compositions or in tablet or capsule form for reducing or maintaining the weight of a subject, one of skill in the art will appreciate that the scope of the invention extends to the treatment of diseases often associated with obesity.

Moreover, the present invention also provides for the addition of weight-reducing or weight-maintaining amounts of these compounds to food items such as, for example, beverages, frozen desserts, sauces, snacks, cereals and the like. Likewise, in this manner, the weight-gaining effects of such items can often be reversed or reduced. For example, the present invention also includes the addition of a $C_{12}$–$C_{15}$ fatty acid and/or its derivatives to a beverage such as a soda (of either the sugared or low- or non-calorie variety).

The following experimental results are offered by way of example and are not meant to limit the scope of the invention.

EXAMPLES

Example 1

This example illustrates the weight-reducing activity of myristic acid in animals.

Methods 1.1 Experimental Protocol

Mice of both sexes and from three different strains (Jackson Laboratories, Bar Harbor, Me.) were fed myristic acid (95% myristic acid, Hystrene, Witco, Memphis Tenn.) in peanut butter (Jiffy Light Creamy Peanut Butter) for five consecutive days. The mouse is a well recognized model for both mechanistic and therapeutic studies of human obesity (Pelleymounter et al., *Science*, 269:540–543 1995. The animals were randomized to one of five dosing groups: 0 (control), 0.1, 1.0, 10, 1000 mg/kg of myristic acid in 1/16 tsp. peanut butter. All measurements were performed by an independent investigator blinded to grouping. Daily measurements included: animals weight, food and water consumption, bedding weight (for urine and feces) and standard behavioral measures of activity and aggressive behavior.

1.2 Statistical Analysis

Data were compared using multivariate analysis of variance (MANOVA) for weight change as a function of diet. Additional step-wise multiple regression analyses were performed for effect of dose of myristic acid on weight loss.

Results

Eighteen animals were entered into the study. The dose of myristic acid was significantly correlated with weight reduction (r=0.62; p=0.002). Of these, two animals did not consume the study food mixture and thus, they were not subjected to the myristic acid effects. When the remaining 16 animals are analyzed separately, the dose of myristic acid remained significantly correlated with weight loss (r=0.60; p=0.014). As would be expected with a high calorie regimen, the control animals gained weight. The animals receiving myristic acid at doses of 10 and 1000 mg/kg demonstrated a significant reduction in body weight when compared to baseline. The animals receiving the 0.1 mg/kg dose of myristic acid maintained their weight and the animals receiving 1 mg/kg myristic acid gained weight similar to control animals. These results are summarized in Table 1.

There were no significant differences between groups with respect to food and water consumption, waste production or behavioral indices.

TABLE 1

Weight Reduction by Myristic Acid Dose

|  | Control | 0.1 mg/kg | 1.0 mg/kg | 10 mg/kg | 1000 mg/kg |
|---|---|---|---|---|---|
| Baseline | 39.5 ± 0.9 | 40.4 ± 2.3 | 39.9 ± 3.0 | 46.1 ± 2.4 | 40.8 ± 0.8 |
| One week | 41.0 ± 0.9 | 40.5 ± 2.0 | 41.5 ± 2.9 | 45.3 ± 3.1 | 40.2 ± 1.5 |
| Weight change | 1.5 ± 0.2 | 0.1 ± 0.7 | 1.6 ± 0.2 | −0.8 ± 0.5 | −0.6 ± 0.9 |
| % Weight change | 3.8% | +0.2% | +4.0% | −1.8% | −1.5% |
| Change v. control | — | −3.6% | +0.2% | −5.6% | −5.1% |

In this study, myristic acid given orally caused weight reduction in a dose-related manner in mice, independent of sex or strain. The weight reduction effects were found with doses from 10 to 1000 mg/kg. The effect of the lowest dose indicated that animals could maintain their baseline weight despite high calorie dietary supplementation. There were no differences in water consumption or weight production and behavioral measures such as activity were not affected by myristic acid.

These findings are consistent with a direct effect of myristic acid on metabolism. Myristic acid is known to have a direct effect which leads to an altering of oxidative metabolism. DeGrella and Light demonstrated that myristic acid reduced the efficiency of oxidative phosphorylation in isolated cardiac cells, especially in comparison to other fatty acids. (see DeGrella et al., *J. Biol. Chem.* 255:20:9731 (1992)) Myristic acid also differed from other fatty acids in its effects on glucose metabolism. Stucki and colleagues have also reported that fatty acids regulate the efficiency of oxidative phosphorylation and that low concentrations of fatty acids such as myristic acid, could possibly decouple oxidative phosphorylation. (see Stucki et al., *Journal of Biological Chemistry*, 264:6376 (1989)).

Stucki et al. further demonstrated that fatty acids, including myristic acid, can modify isolated mitochondrial proteins via a novel form of reversible acylation. The authors suggested that acylation of mitochondrial proteins is important for the regulation of the degree of coupling of oxidative phosphorylation.

This uncoupling effect is similar to that ascribed to endogenous molecules in brown fat. Others have described the potential role of brown fat in the development of morbid obesity and have also implicated that the relative uncoupling energy consumption from energy production may be important to body weight. Yet efforts to utilize the endogenous protein thermogenin to directly alter metabolism and body weight have not been successful. Proteins, such as thermogenin, are not readily transported into cells and mitochondria. Yet, elucidation of the potential role of these endogenous uncouplers in weight loss has proven difficult (Friedman, et al., *Cell*, 69:217 (1992)).

The approach to weight reduction uses dietary supplementation with myristic acid to directly alter metabolism. Myristic acid has no known hormonal activity and thus directly alters body weight without causing other physiologically significant side effects. There was no evidence of toxic effects at any of the dosing levels of myristic acid.

The weight reducing effects can be obtained from any substance from which myristic acid (also known as myristate) can become biologically available. Examples of these substances include (but are not limited to) combinations of myristic acid and its salts and substances from which myristic acid can be generated by chemical hydrolysis, esterases, proteases and redox reactions. Indeed, others have demonstrated that myristic acid, dimethyl myristamide or beta-hydroxymyristic acid did not result in notable toxicity (see Bradley, *Proceedings of the Society for Experimental Medicine and Biology*, 151:267 (1976)). In addition, prior exposure to myristic acid-protein complexes renders animals resistant to a dose of bacterial endotoxin that is otherwise lethal for untreated animals (see, Bradley, ibid.).

What is claimed is:

1. A method for reducing weight in a subject in need thereof, said method comprising administering to said subject a composition comprising a weight-reducing amount of a compound selected from the group consisting of a $C_{12}$–$C_{15}$ fatty acid, and metal ion salts of a $C_2$–$C_{15}$ fatty acid.

2. A method for reducing weight in a subject in need thereof, said method comprising administering to said subject a composition comprising a weight-reducing amount of myristic acid.

3. A method in accordance with claim 1, wherein said subject is mammalian.

4. A method in accordance with claim 1, wherein said subject is human.

5. A method in accordance with claim 1, wherein said composition is formulated as a dietary supplement in unit dosage form.

6. A method in accordance with claim 1, wherein said composition is formulated as a dietary supplement in unit dosage form in tablets, pills or capsules.

7. A method for reducing weight in a human, said method comprising ingesting a compound selected from the group consisting of a $C_{12}$–$C_{15}$ fatty acid, and metal ion salts of a $C_{12}$–$C_{15}$ fatty acid, in an amount of from about 0.1 mg per kg of said human per day to about 10,000 mg per kg of said human per day.

8. A method in accordance with claim 7, wherein said fatty acid is myristic acid.

9. A method in accordance with claim 7, wherein said amount is from about 10 mg per kg of said human per day to about 1000 mg per kg of said human per day.

10. A method, for reducing weight in a human, said method comprising ingesting a compound, wherein said compound is a lower alkyl ester of a $C_{12}$–$C_{15}$ fatty acid and is ingested in an amount of from about 10 mg per kg of said human per day to about 1000 mg per kg of said human per day.

11. A method of reducing weight in a subject, said method comprising supplementing the diet of said subject with an orally administered formulation of a $C_{12}$–$C_{15}$ fatty acid in unit dosage form.

12. A method in accordance with claim 11, wherein said fatty acid is myristic acid.

13. A method in accordance with claim 11, wherein said subject is human.

14. A method of maintaining the weight of a subject, said method comprising administering to said subject, a weight-maintaining amount of a compound selected from the group consisting of a $C_{12}$–$C_{15}$ fatty acid, and metal ion salts of a $C_{12}$–$C_{15}$ fatty acid.

15. A method in accordance with claim 14, wherein said fatty acid is myristic acid.

16. A method in accordance with claim 14, wherein said weight-maintaining amount is from about 0.05 mg per kg of said subject per day to about 10 mg per kg of said subject per day.

17. A method for reducing weight in a subject in need thereof, said method comprising administering to said subject a compound which is:

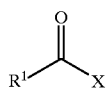 (I)

wherein $R_1$ is a hydrocarbon chain having a molecular length equivalent to a $C_{11}$ to $C_{14}$ fatty acid, which chain optionally contains a lower alkyl ($C_1$–$C_4$) group; and wherein X is —OH, —OR, —NH$_2$, —NHR, —NRR', —NHOH, —NHOR, in which R and R' are each independently a lower alkyl group having from one to eight carbon atoms, or wherein R and R' can be combined to form a ring structure, which is optionally substituted by a lower alkyl ($C_1$–$C_4$) group.

18. A method in accordance with claim 1, wherein said metal ion salt of a $C_{12}$–$C_{15}$ fatty acid is a metal ion salt of myristic acid.

* * * * *